United States Patent
Dieckman et al.

(10) Patent No.: US 12,214,163 B2
(45) Date of Patent: Feb. 4, 2025

(54) INFUSION PUMP CONTROL UNIT KEYPAD

(71) Applicant: CareFusion 303, Inc., San Diego, CA (US)

(72) Inventors: James Dieckman, San Diego, CA (US); Raphael Lozano, San Diego, CA (US); Hao Ton-That, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/775,579

(22) Filed: Jul. 17, 2024

(65) Prior Publication Data

US 2024/0366871 A1 Nov. 7, 2024

Related U.S. Application Data

(63) Continuation of application No. 17/514,794, filed on Oct. 29, 2021, now Pat. No. 12,064,598.

(60) Provisional application No. 63/140,137, filed on Jan. 21, 2021.

(51) Int. Cl.
*F21V 23/04* (2006.01)
*A61M 5/172* (2006.01)
*F21V 31/00* (2006.01)
*G06F 3/02* (2006.01)

(52) U.S. Cl.
CPC ............ *A61M 5/172* (2013.01); *F21V 23/04* (2013.01); *F21V 31/005* (2013.01); *A61M 2205/502* (2013.01); *A61M 2205/587* (2013.01); *A61M 2207/10* (2013.01); *G06F 3/0202* (2013.01)

(58) Field of Classification Search
CPC ..... F21V 23/04; F21V 31/005; H01H 13/702; H04B 1/202; H04B 345/17; A61M 5/172
See application file for complete search history.

(56) References Cited

U.S. PATENT DOCUMENTS

| | | | |
|---|---|---|---|
| 5,856,641 | A | 1/1999 | Schreiber |
| 7,872,642 | B2 | 1/2011 | Hayes |
| 8,038,593 | B2 | 10/2011 | Friedman et al. |
| 8,415,570 | B2 | 4/2013 | Dabov et al. |
| 9,415,175 | B2 | 8/2016 | Vanderveen et al. |
| 10,313,497 | B2 | 6/2019 | Hobson et al. |
| 10,651,879 | B2 | 5/2020 | Hobson et al. |

(Continued)

OTHER PUBLICATIONS

International Search Report and Written Opinion for Application No. PCT/US2021/058825, dated Mar. 2, 2022, 13 pages.

*Primary Examiner* — Joseph L Williams
(74) *Attorney, Agent, or Firm* — Morgan, Lewis & Bockius LLP

(57) ABSTRACT

Infusion systems are provided that include an infusion pump and a fluid ingress protection assembly. The fluid ingress protection assembly includes a cover assembly having an outer surface and an inner surface, a perimeter gasket disposed within a raised perimeter on the outer surface of the cover assembly, a lens coupled to the outer surface of the cover assembly, a circuit assembly coupled to the outer surface of the cover assembly, a switch assembly coupled to the circuit assembly, a shield assembly coupled to the switch assembly, the shield assembly comprising an electrostatic discharge shield and an overlay assembly coupled with the shield assembly. Methods of assembling an infusion system are also provided.

20 Claims, 6 Drawing Sheets

(56) References Cited

U.S. PATENT DOCUMENTS

| | | |
|---|---|---|
| 10,869,963 B2 | 12/2020 | Zhang |
| 2004/0257727 A1 | 12/2004 | Chu |
| 2007/0299389 A1 | 12/2007 | Halbert et al. |
| 2012/0092264 A1 | 4/2012 | Cheney, II et al. |
| 2014/0017543 A1* | 1/2014 | Fonacier ................ G06F 3/023 |
| | | 429/100 |
| 2014/0066851 A1* | 3/2014 | Cheney, II ............ H03M 11/04 |
| | | 341/23 |
| 2014/0104792 A1 | 4/2014 | Jerziorek |
| 2020/0341559 A1 | 10/2020 | Wang et al. |

* cited by examiner

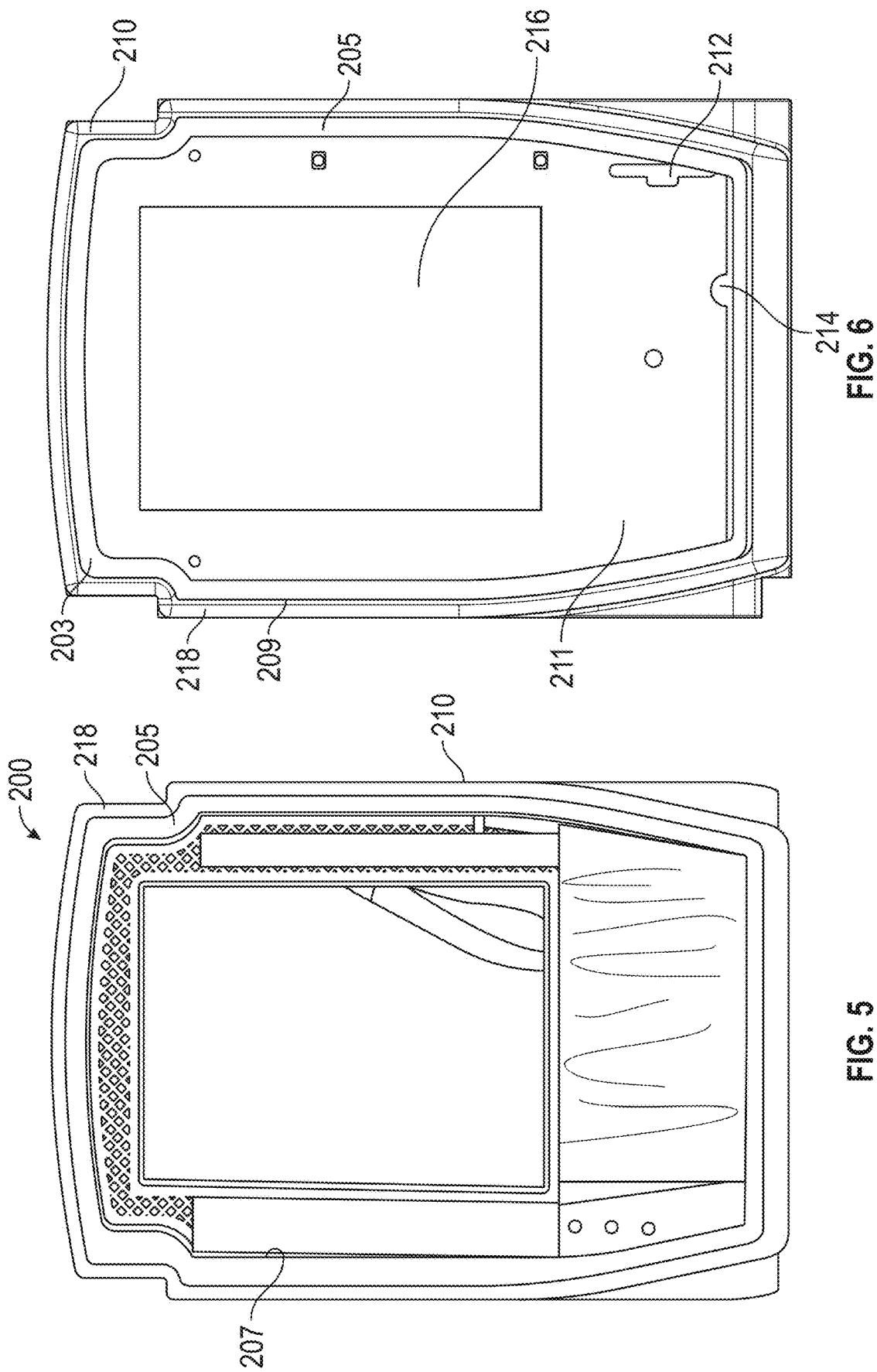

INFUSION PUMP CONTROL UNIT KEYPAD

CROSS-REFERENCE TO RELATED APPLICATION

This application is a continuation of U.S. patent application Ser. No. 17/514,794 entitled "INFUSION PUMP CONTROL UNIT KEYPAD," filed on Oct. 29, 2021, issued as U.S. Patent No. 12,064,598 on Aug. 20, 2024, which claims the benefit of U.S. Provisional Patent Application No. 63/140,137 entitled "INFUSION PUMP CONTROL UNIT KEYPAD," filed on Jan. 21, 2021, the disclosure of which are hereby incorporated by reference in their entirety for all purposes.

TECHNICAL FIELD

The present disclosure generally relates to infusion pumps, in particular infusion pump control unit keypads with fluid ingress protection.

BACKGROUND

In typical infusion pump design, a pump control unit has a keypad for entry of information and control of pump settings by a user. The typical pump control unit keypad has multiple layers of components such as overlays, protective liners, circuit layers, etc., all stacked together like a sandwich. However, the typical combination of components provides seams or gaps that can allow fluid ingress. As infusion pumps are consistently used in medical settings, such as operating rooms and hospital rooms, these infusion pumps are routinely cleaned with liquids. Accordingly, the typical pump control unit keypad suffers from fluid ingress into the internal components, resulting in corrosion and damage to metal components, electronic components and flex cables. This results in costly repairs and replacements of infusion pump components.

For these reasons, it is desirable to provide pump control unit keypads that prevent fluid ingress under standard operating conditions, thus improving the life cycle and reliability of infusion pumps while reducing repair costs.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

FIG. 5 depicts a front view of a pump control unit keypad without a top overlay, according to aspects of the disclosure.

FIG. 6 depicts a front view of a pump control unit keypad front cover and gasket assembly, according to aspects of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
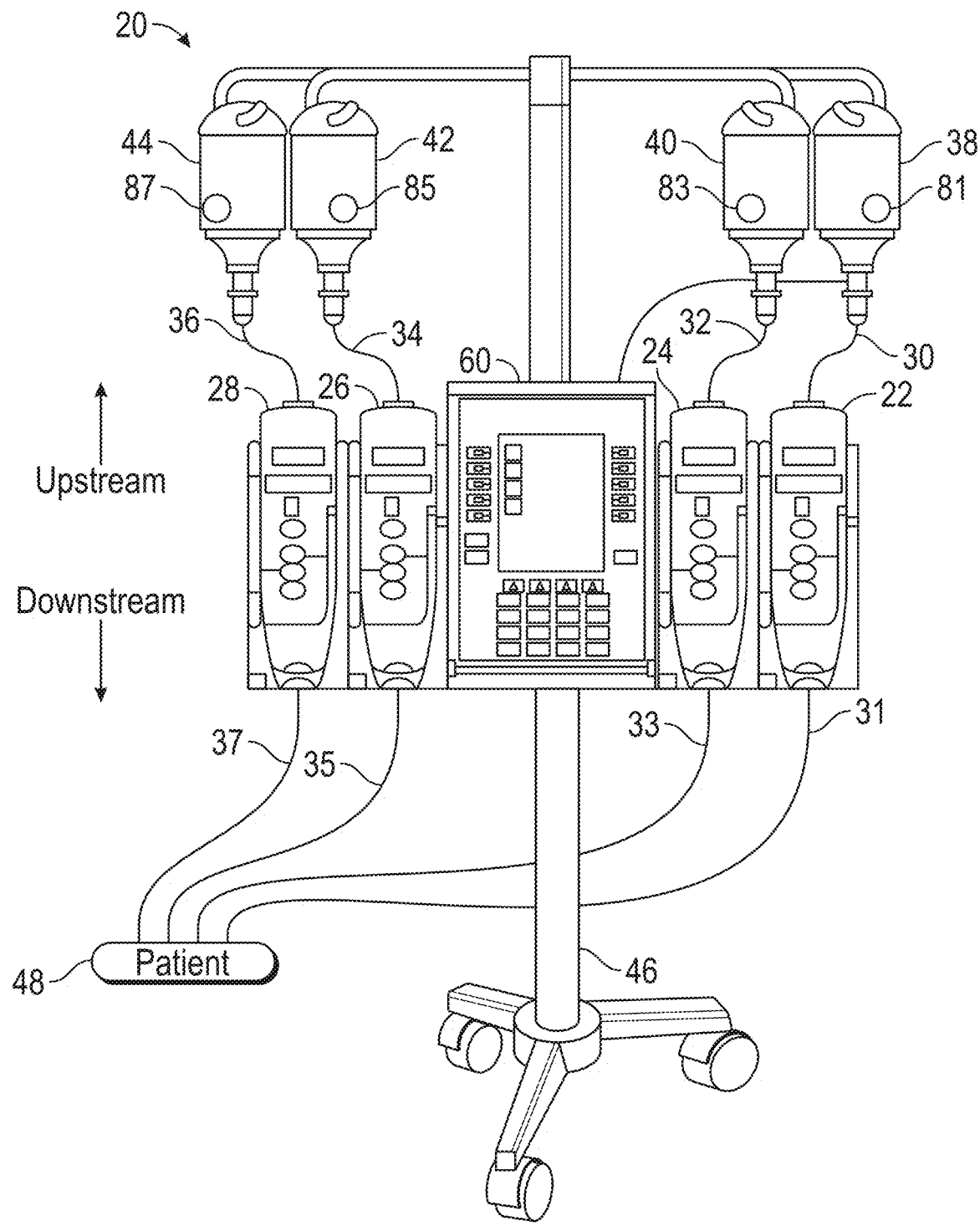
FIG. 1 depicts a perspective view of an example patient care system having a pump control unit and four fluid infusion pumps, each of which is connected to a respective fluid supply for pumping the contents of the fluid supply to a patient, according to some aspects of the disclosure.

Referring now in more detail to the drawings in which like reference numerals refer to like or corresponding elements among the several views, there is shown in FIG. 1 a patient care system 20 having four infusion pumps 22, 24, 26, and 28 each of which is fluidly connected with an upstream fluid line 30, 32, 34, and 36, respectively. Each of the four infusion pumps 22, 24, 26, and 28 is also fluidly connected with a downstream fluid line 31, 33, 35, and 37, respectively. The fluid lines can be any type of fluid conduit, such as an IV administration set, through which fluid can flow through. It should be appreciated that any of a variety of pump mechanisms can be used including syringe pumps.

Fluid supplies 38, 40, 42, and 44, which may take various forms but in this case are shown as bottles, are inverted and suspended above the pumps. Fluid supplies may also take the form of bags or other types of containers including syringes. Both the patient care system 20 and the fluid supplies 38, 40, 42, and 44 are mounted to a roller stand, IV pole 46, table top, etc.

A separate infusion pump 22, 24, 26, and 28 is used to infuse each of the fluids of the fluid supplies into the patient. The infusion pumps are flow control devices that will act on the respective fluid line to move the fluid from the fluid supply through the fluid line to the patient 48. Because individual pumps are used, each can be individually set to the pumping or operating parameters required for infusing the particular medical fluid from the respective fluid supply into the patient at the particular rate prescribed for that fluid by the physician. Such medical fluids may include drugs or nutrients or other fluids. The infusion pumps 22, 24, 26, and 28 are controlled by a pump control unit 60.

Fluid supplies 38, 40, 42, and 44 are each coupled to an electronic data tag 81, 83, 85, and 87, respectively, or to an electronic transmitter. Any device or component associated with the infusion system may be equipped with an electronic data tag, reader, or transmitter.

Typically, medical fluid administration sets have more parts than are shown in FIG. 1. Many have check valves, drip chambers, valves with injection ports, connectors, and other devices well known to those skilled in the art. These other devices have not been included in the drawings so as to preserve clarity of illustration.

Figure 2:
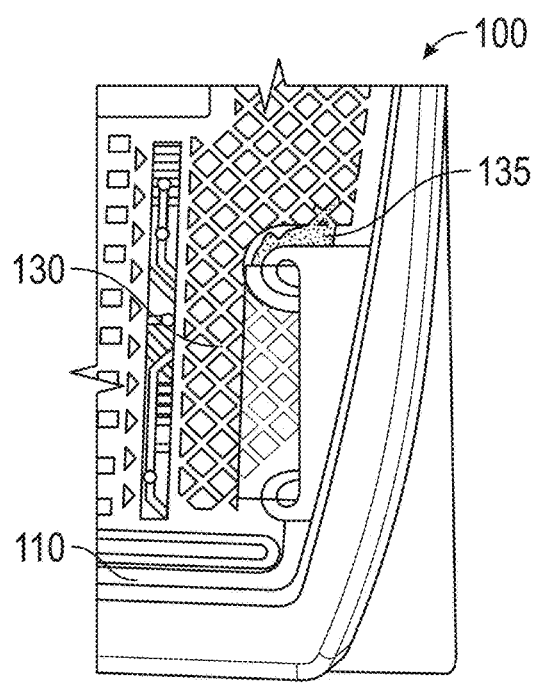
FIG. 2 depicts a front view of an internal pump control unit keypad component showing corrosion damage from fluid ingress.
Figure 3:
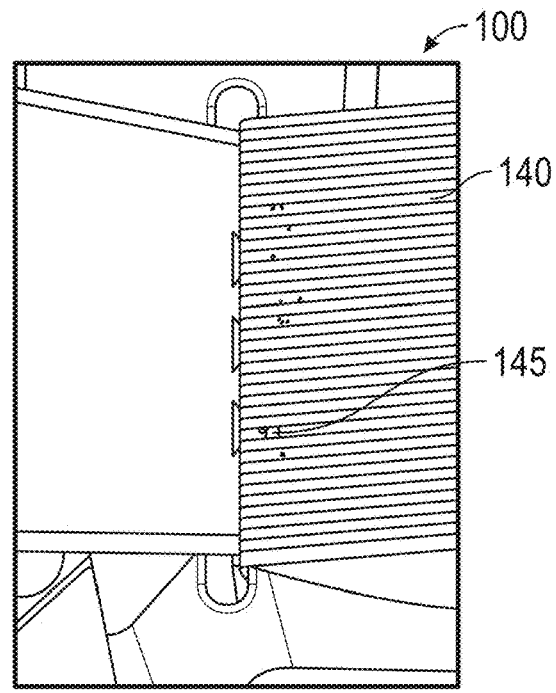
FIG. 3 depicts a rear view of an internal pump control unit keypad cable showing corrosion damage from fluid ingress.
Figure 4:
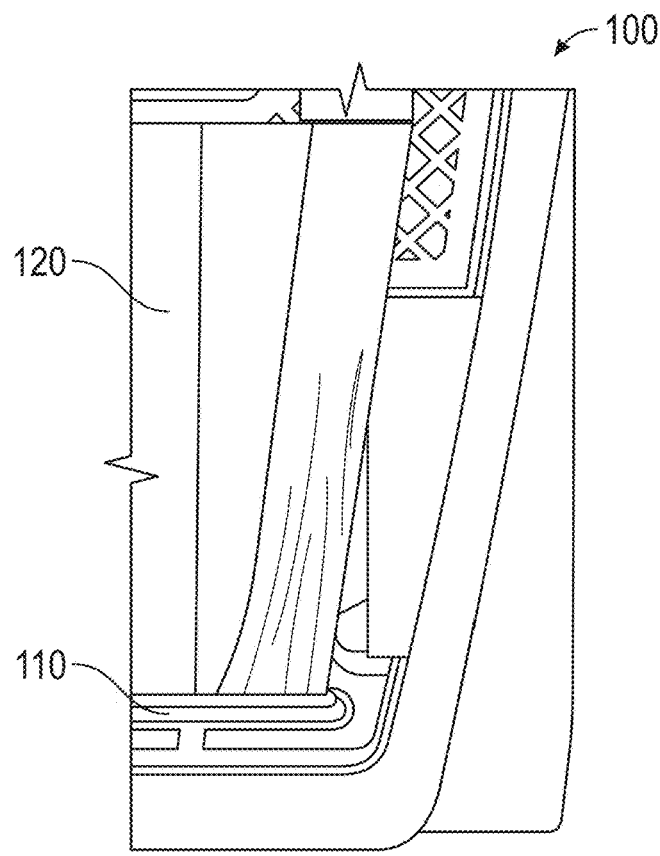
FIG. 4 depicts a front view of a portion of a typical pump control unit keypad without a top overlay, according to aspects of the disclosure.

Turning now to FIGS. 2-4, a typical pump control unit keypad 100 includes fillers 110 that are used to ensure that a keypad overlay (not shown) fits over the internal keypad assembly 120 without damage to either the keypad overlay or the internal keypad assembly 120. The use of the fillers 110 typically results in seams and/or gaps between the keypad overlay and the internal keypad assembly 120, thus allowing for fluid ingress into the pump control unit keypad 100. For example, as shown in FIG. 2, a component layer 130 (e.g., electrostatic discharge (ESD) shield) has corrosion damage 135 due to fluid ingress into the pump control unit keypad 100. As another example, as shown in FIG. 3, an internal cable 140 (e.g., flex tail cable) also has corrosion damage 145 due to fluid ingress into the pump control unit keypad 100. Such corrosion damage typically will cause the internal keypad assembly 120 to fail, requiring repair or replacement of the pump control unit keypad 100.

Turning now to FIGS. 5-8, pump control unit keypad assembly 200 is shown according to aspects of the disclosure. As shown in FIGS. 6, pump control unit keypad assembly 200 includes a gasket 205 (e.g., full perimeter gasket) disposed on a front cover assembly 210. Here, the gasket 205 provides a full perimeter seal against an overlay 215 (see FIG. 8) when the overlay 215 is coupled to the front cover assembly 210 and gasket 205. The gasket 205 eliminates the need for fillers 110 as the gasket 205 itself provides a seat for the overlay 215 that keeps the overlay 215 from damaging, cracking or crushing the remaining components of the pump control unit keypad assembly 200. Further, since the gasket 205 provides a full perimeter seal against the overlay 215, there are no seams of gaps that allow for fluid ingress into the pump control unit keypad assembly 200. Thus, the pump control unit keypad assembly 200 may be freely sprayed and/or cleaned with liquids without incurring the corrosion issues discussed above.

Figure 7:
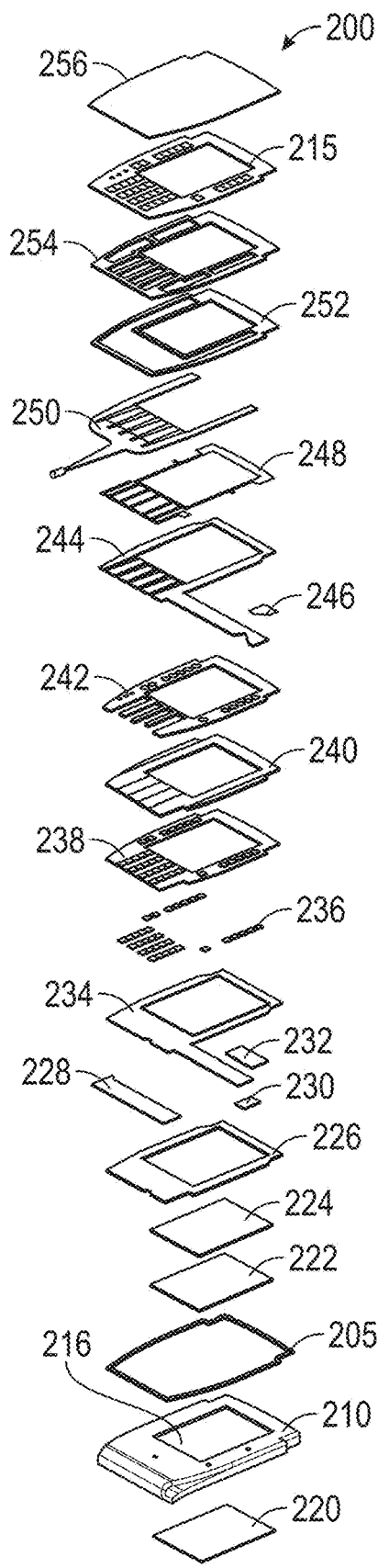
FIG. 7 depicts an exploded perspective view of a pump control unit keypad assembly, according to aspects of the disclosure.
Figure 8:
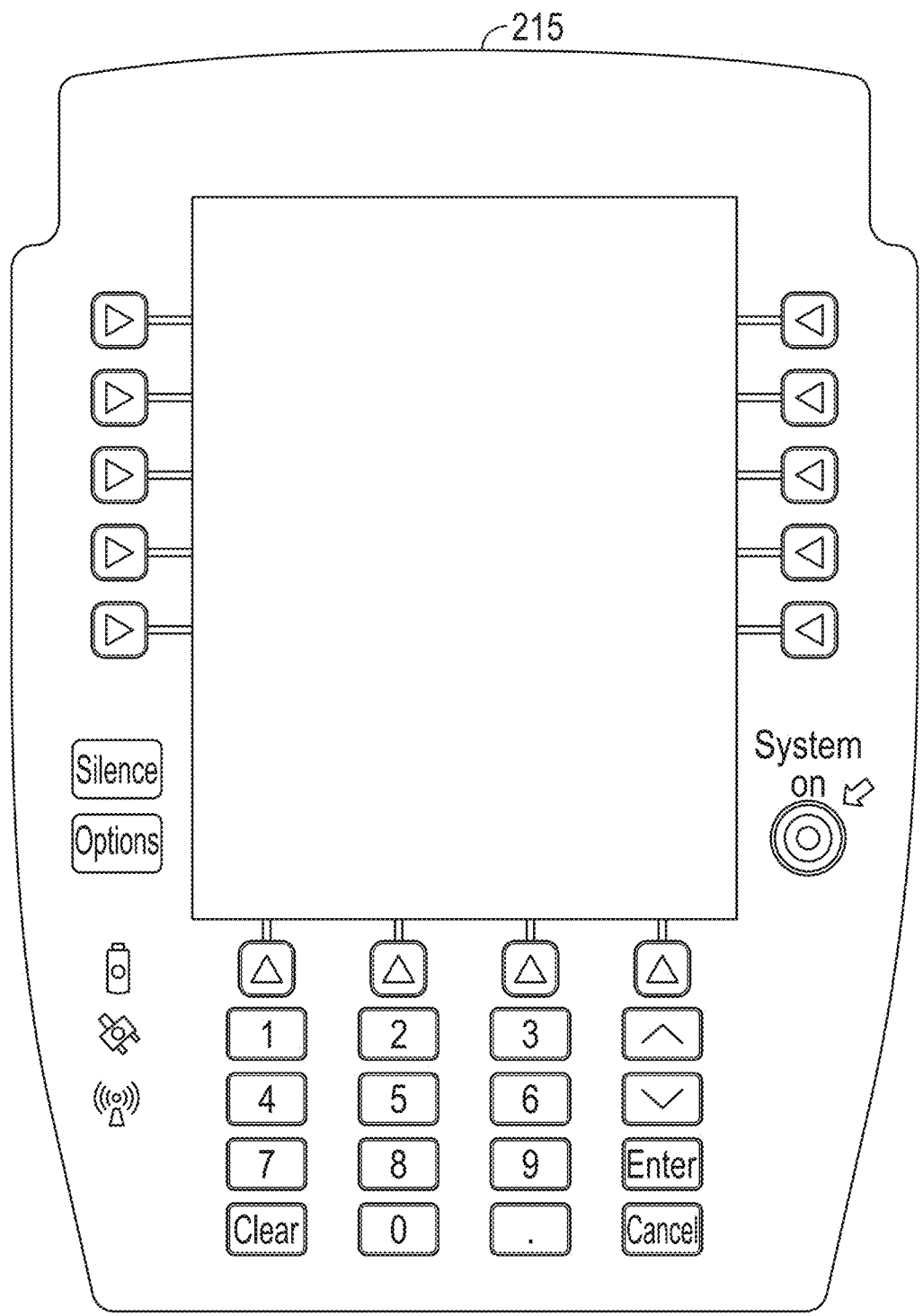
FIG. 8 depicts a front view of a pump control unit keypad overlay, according to aspects of the disclosure.

As shown in FIG. 7, the pump control unit keypad assembly 200 includes many components that are stacked or sandwiched together to form the complete assembly 200. A rear protective liner 220 may be disposed on the back or internal side of the front cover assembly 210, the rear protective liner 220 disposed within or covering a window 216 in the front cover assembly 210. The gasket 205 is disposed on the front or external facing side 211 of the front cover assembly 210, inside a raised perimeter 218 of the front cover assembly 210. Stacked upward or outward from the front cover assembly 210 are a lens 222, an adhesive layer 224 (e.g., optically clear adhesive), a rear adhesive 226, a metal layer 228 (e.g., Mylar™), a printed circuit board (PCB) connector 230, a polycap 232, a circuit layer 234, multiple semiconductor switch domes 236, a dome spacer 238, a dome overlay 240, a shielding adhesive 242, an ESD shield 244 with a tail stiffener 246, a light source adhesive 248, a light source 250 (e.g., fiber optic lamp), a light block 252, an overlay adhesive 254, the overlay 215 and a protective liner 256.

The stack of components from the lens 222 to the light block 252 are sized and shaped to fit within an inner perimeter 207 of the gasket 205, for a portion of the component (e.g., a tail of the circuit layer 234, tail of the ESD shield 244, tail of the light source 250) to extend past an outer perimeter 209 of the gasket 205 through openings 212, 214 on the front cover assembly 210, or for a portion of the component (e.g., a tail of the circuit layer 234 or the ESD shield 244) to extend past an outer perimeter 209 of the gasket 205 between the gasket 205 and the front cover assembly 210. No portion of any of the components of the pump control unit keypad assembly 200 extends over the outer surface 203 of the gasket 205, and thus no portion of any of the components of the pump control unit keypad assembly 200 come between the outer surface 203 of the gasket 205 and the overlay 215. The result is a liquid proof or resistant seal between the outer surface 203 of the gasket 205 and the overlay 215 around the entire perimeter of the gasket 205.

In some aspects of the disclosure, a membrane switch may be used in place of any combination of the above described components. In some aspects of the disclosure, the gasket 205 may have a height that equals or exceeds the combined height of the outer perimeter of the stack of components from the lens 222 to the light source 250 or the light block 252. In aspects of the disclosure, the pump control unit keypad assembly 200 is configured to provide venting (e.g., via vent holes), to work for 200,000 keypresses, to operate in a temperature range of 41-104 degrees Fahrenheit, as well as to withstand storage temperature, humidity and pressure.

In aspects of the disclosure, the light source 250 may have asymmetrical panels where a wider panel may be used to provide increased illumination over a narrower panel. In aspects of the disclosure, the gasket 205 may be formed of any suitable material (e.g., rubber, silicone).

Figure 9:
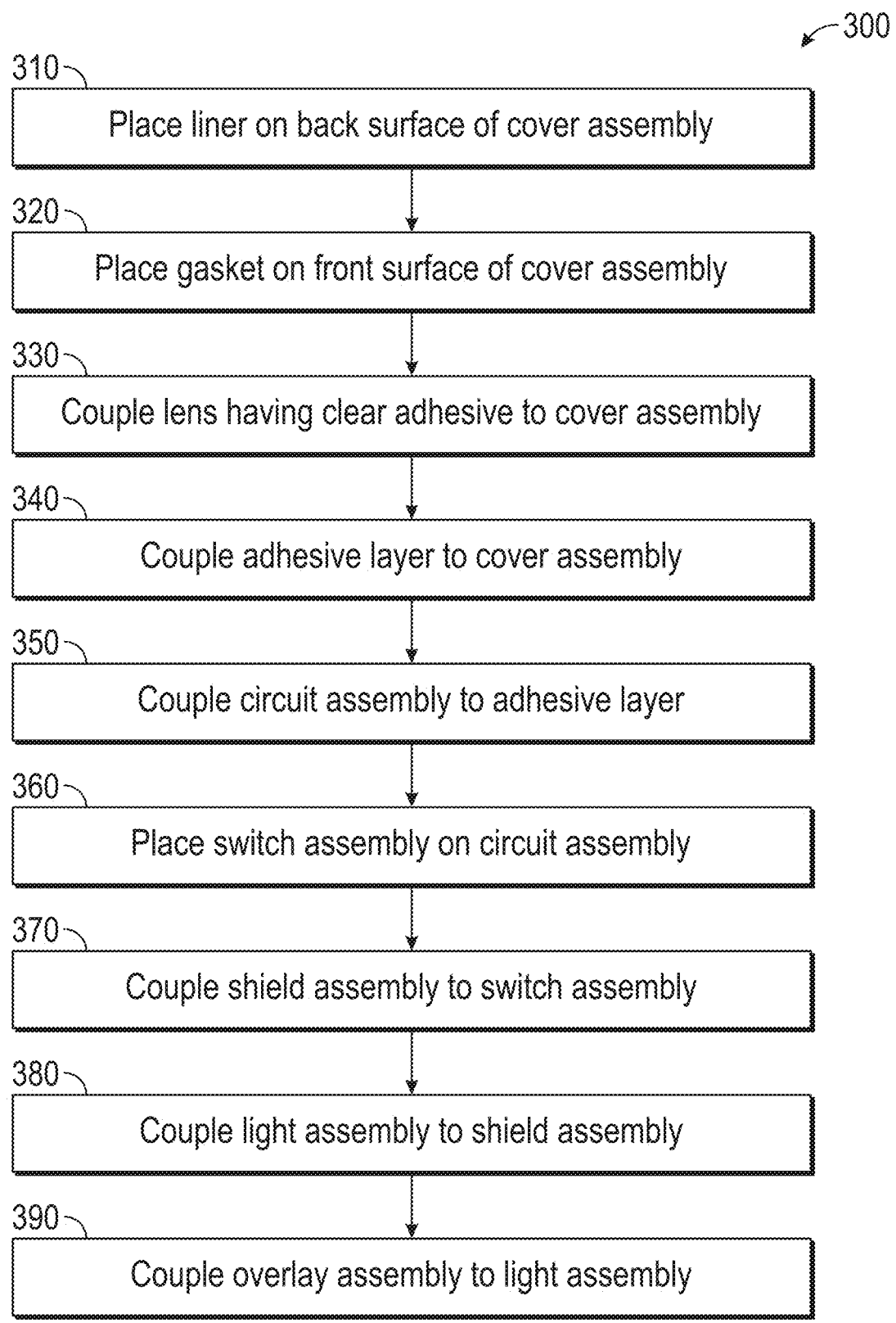
FIG. 9 illustrates a method of making a pump control unit keypad assembly, according to aspects of the disclosure.

According to some aspects of the disclosure, a method 300 of making a pump control unit keypad assembly 200 is shown in FIG. 9. In step 310, a protective liner (e.g., rear protective liner 220) is placed on a back surface of a cover assembly (e.g., front cover assembly 210). A gasket (e.g., gasket 205) is placed on the cover assembly (e.g., within a raised perimeter of front cover assembly 210), in step 320. In step 330, a lens having an adhesive (e.g., lens 222 and optically clear adhesive layer 224) is coupled to the cover assembly. An adhesive (e.g., rear adhesive 226) is coupled to the cover assembly, in step 340.

In step 350, a circuit assembly (e.g., metal layer 228, PCB connector 230, polycap 232, circuit layer 234) are coupled to the adhesive. Here, a portion of the circuit assembly (e.g., tail of circuit layer 234) may be fed or poked through a cover assembly opening (e.g., opening 212). A switch assembly (e.g., semiconductor switch domes 236, dome spacer 238, dome coverlay 240) are placed on the circuit components, in step 360. In step 370, a shield assembly (e.g., shielding adhesive 242, ESD shield 244, tail stiffener 246) are coupled to the switch assembly. Here, a portion of the shield assembly (e.g., tail of ESD shield 244) may be fed or poked through a cover assembly opening (e.g., opening 212).

A light assembly (e.g., light source adhesive 248, light source 250, light block 252) are coupled to the shield assembly, in step 380. Here, a portion of the light assembly (e.g., tail of light source 250) may be fed or poked through a cover assembly opening (e.g., opening 214). In step 390, an overlay assembly (e.g., overlay adhesive 254, overlay 215, protective liner 256) is coupled to the light assembly.

In some embodiments, an infusion system comprises an infusion pump and a fluid ingress protection assembly. The fluid ingress protection assembly includes a cover assembly having an outer surface and an inner surface, a perimeter gasket disposed within a raised perimeter on the outer surface of the cover assembly, a lens coupled to the outer surface of the cover assembly, a circuit assembly coupled to the outer surface of the cover assembly, a switch assembly coupled to the circuit assembly, a shield assembly coupled to the switch assembly, the shield assembly comprising an electrostatic discharge shield and an overlay assembly coupled with the shield assembly.

In aspects of the disclosure, a protective liner is coupled to one of the inner surface of the cover assembly and the lens. In aspects of the disclosure, an optically clear adhesive is coupled to the lens. In aspects of the disclosure, the circuit assembly comprises: a metal layer; a printed circuit board connector; a polycap; and a circuit layer. In aspects of the disclosure, the circuit assembly is coupled to the cover assembly by an adhesive layer. In aspects of the disclosure, the switch assembly comprises: a plurality of semiconductor switch domes; a dome spacer; and a dome coverlay. In aspects of the disclosure, the switch assembly comprises a membrane switch. In aspects of the disclosure, the shield assembly comprises: an electrostatic shield; and a tail stiffener.

In aspects of the disclosure, the shield assembly is coupled to the switch assembly by an adhesive layer. In aspects of the disclosure, the light assembly comprises: a fiber optic lamp; and a light block layer. In aspects of the disclosure, the light assembly is coupled to the shield assembly by an adhesive layer. In aspects of the disclosure, the overlay assembly comprises: an overlay; and a protective liner. In aspects of the disclosure, the overlay assembly is coupled to the light assembly by an adhesive layer. In aspects of the disclosure, a tail portion of the circuit assembly and a tail portion of the shield assembly are disposed through an opening in the cover assembly past the inner surface of the cover assembly. In aspects of the disclosure, a tail portion of the light assembly is disposed through an opening in the cover assembly past the inner surface of the cover assembly.

In some embodiments, a method of assembling an infusion system includes assembling a fluid ingress protection assembly by: placing a gasket within a raised perimeter of an outer surface of a cover assembly; coupling a lens and an optically clear adhesive to a window of the cover assembly; coupling a circuit assembly to the outer surface of the cover assembly with a rear adhesive layer; coupling a switch assembly to the circuit assembly; coupling a shield assembly to the switch assembly with a shielding adhesive layer, the shield assembly comprising an electrostatic discharge shield; and coupling an overlay assembly to the shield assembly with an overlay adhesive layer; and coupling the fluid ingress protection assembly to a pump control unit.

In aspects of the disclosure, the method comprises coupling a protective lining to one of the lens and an inner surface of the cover assembly over the window. In aspects of the disclosure, the method comprises feeding a tail section of the circuit assembly and a tail section of the shield assembly from the outer surface of the cover assembly through an opening in the cover assembly and past an inner surface of the cover assembly. In aspects of the disclosure, the method comprises feeding a tail section of the light assembly from the outer surface of the cover assembly through an opening in the cover assembly and past an inner surface of the cover assembly. In aspects of the disclosure, the method comprises engaging an outer surface of an entire perimeter of the gasket to an inner surface of the overlay assembly to provide a fluid tight fit against fluid ingress from external fluid sources.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, inserting and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

In any embodiment, data can be forwarded to a "remote" device or location," where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Some embodiments include implementation on a single computer, or across a network of computers, or across networks of networks of computers, for example, across a network cloud, across a local area network, on hand-held computer devices, etc. The computers may be physical machines or virtual machines hosted by other computers. In certain embodiments, one or more of the steps described herein are implemented on a computer program(s). Such computer programs execute one or more of the steps described herein. In some embodiments, implementations of the subject method include various data structures, categories, and modifiers described herein, encoded on computer-readable medium(s) and transmissible over communications network(s).

Software, web, internet, cloud, or other storage and computer network implementations of the present invention could be accomplished with standardized programming techniques specifically adapted to cause one or more device to perform the various assigning, calculating, identifying, scoring, accessing, generating or discarding steps described.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An infusion system comprising:
an infusion pump; and a fluid ingress protection assembly including:
   a cover assembly having an outer surface and an inner surface;
   a perimeter gasket disposed within a raised perimeter on the outer surface of the cover assembly;
   a lens coupled to the outer surface of the cover assembly;
   a circuit assembly coupled to the outer surface of the cover assembly;
   a switch assembly coupled to the circuit assembly;
   a shield assembly coupled to the switch assembly, the shield assembly comprising an electrostatic discharge shield; and
   an overlay assembly coupled with the shield assembly.

2. The infusion system of claim 1, further comprising a patient care unit including a connector to receive the infusion pump.

3. The infusion system of claim 2, wherein the patient care unit further includes a keypad, and wherein the fluid ingress protection assembly is included in the patient care unit.

4. The infusion system of claim 1, wherein the infusion pump includes a keypad, and wherein the fluid ingress protection assembly is included in the infusion pump.

5. The infusion system of claim 1, wherein the fluid ingress protection assembly, further comprises:
   a protective liner coupled to one of the inner surface of the cover assembly and the lens.

6. The infusion system of claim 1, wherein the fluid ingress protection assembly further comprises:
   an optically clear adhesive coupled to the lens.

7. The infusion system of claim 1, wherein the circuit assembly comprises:
   a metal layer;
   a printed circuit board connector;
   a polycap; and
   a circuit layer.

8. The infusion system of claim 1, wherein the circuit assembly is coupled to the cover assembly by an adhesive layer.

9. The infusion system of claim 1, wherein the switch assembly comprises:
   a plurality of semiconductor switch domes;
   a dome spacer; and
   a dome overlay.

10. The infusion system of claim 1, wherein the switch assembly comprises a membrane switch.

11. The infusion system of claim 1, wherein the shield assembly comprises:
   a tail of the electrostatic discharge shield; and
   a tail stiffener.

12. The infusion system of claim 1, wherein the overlay assembly comprises:
   an overlay; and
   a protective liner.

13. The infusion system of claim 1, further comprising a light assembly, wherein the overlay assembly is coupled to the light assembly by an adhesive layer.

14. The infusion system of claim 1, wherein a tail portion of the circuit assembly and a tail portion of the shield assembly are disposed through an opening in the cover assembly past the inner surface of the cover assembly.

15. The infusion system of claim 1, further comprising a light assembly, wherein a tail portion of the light assembly is disposed through an opening in the cover assembly past the inner surface of the cover assembly.

16. A method of assembling an infusion system, the method comprising:
   assembling a fluid ingress protection assembly by:
     placing a gasket within a raised perimeter of an outer surface of a cover assembly;
     coupling a lens and an optically clear adhesive to a window of the cover assembly;
     coupling a circuit assembly to the outer surface of the cover assembly with a rear adhesive layer;
     coupling a switch assembly to the circuit assembly;
     coupling a shield assembly to the switch assembly with a shielding adhesive layer, the shield assembly comprising an electrostatic discharge shield; and
     coupling an overlay assembly to the shield assembly with an overlay adhesive layer; and
   coupling the fluid ingress protection assembly to a pump control unit.

17. The method of claim 16, further comprising:
coupling a protective lining to one of the lens and an inner surface of the cover assembly over the window.

18. The method of claim 16, further comprising:
feeding a tail section of the circuit assembly and a tail section of the shield assembly from the outer surface of the cover assembly through an opening in the cover assembly and past an inner surface of the cover assembly.

19. The method of claim 16, further comprising:
feeding a tail section of a light assembly from the outer surface of the cover assembly through an opening in the cover assembly and past an inner surface of the cover assembly.

20. The method of claim 16, further comprising:
engaging an outer surface of an entire perimeter of the gasket to an inner surface of the overlay assembly to provide a fluid tight fit against fluid ingress from external fluid sources.

* * * * *